(12) United States Patent
Nakayama et al.

(10) Patent No.: US 8,367,849 B2
(45) Date of Patent: Feb. 5, 2013

(54) PRODUCTION METHOD FOR SULTONE DERIVATIVES

(75) Inventors: Osamu Nakayama, Niigata (JP); Takashi Fukumoto, Niigata (JP); Jyunko Sato, Niigata (JP); Toshiki Endo, Niigata (JP); Hideki Matsuda, Niigata (JP)

(73) Assignee: Kuraray Co., Ltd., Okayama (JP)

( * ) Notice: Subject to any disclaimer, the term of this patent is extended or adjusted under 35 U.S.C. 154(b) by 0 days.

(21) Appl. No.: 13/061,560

(22) PCT Filed: Sep. 2, 2009

(86) PCT No.: PCT/JP2009/065290
§ 371 (c)(1),
(2), (4) Date: Mar. 1, 2011

(87) PCT Pub. No.: WO2010/026974
PCT Pub. Date: Mar. 11, 2010

(65) Prior Publication Data
US 2011/0160465 A1    Jun. 30, 2011

(30) Foreign Application Priority Data
Sep. 2, 2008    (JP) .................................. 2008-224632

(51) Int. Cl.
C07D 327/04    (2006.01)
(52) U.S. Cl. ......................................................... 549/33
(58) Field of Classification Search .................. 549/33
See application file for complete search history.

(56) References Cited

U.S. PATENT DOCUMENTS
7,498,350 B2    3/2009    Gravestock et al.

FOREIGN PATENT DOCUMENTS
JP    2006-515601 A1    6/2006
JP    2007-031355 A     2/2007
JP    2009-096767 A     5/2009

OTHER PUBLICATIONS

Bonini, 1998, Synlett, p. 1411-1413).*
Mar. 1992, Advanced Organic Chemistry: Reactions, Mechanisms and Structure, 4th Edition, John Wiley & Sons, p. 357.*
Zhurnal Organicheskoi Khimii,10 2 (11), 1954-1961 (1966).
Fujigaya et al., "New Photoresist Materials for 157-nm Lithography Poly[Vinylsulfonyl Fluoride-co-4-(1,1,1,3,3,3-hexafluoro-2-hydroxyproply0-styrene] Partially Protected with tert-Butoxycarbonyl," Chem. Mater. (2003), 15, pp. 1512-1517).

Rondestvedt Jr., et al. "Usaturated Sulfonic Acids, H. Reversibility of the Diels-Alder Reaction with Sulfonyl Chlorides and Sulfonamides," Journal of Organic Chemistry (1952): vol. 17, pp. 975-979.
Krutak et al., "Chemistry of Ethenesulfonyl Fluoride; Fluorosulfonylethylation of Organic Compounds," Journal of Organic Chemistry (1979), vol. 44 (22), pp. 3847-3858.
Rondestvedt Jr., et al., "Unsaturated Sulfonic Acids. IV. PReparation and Properties of a-Bromoalkenesulfonyl Chlorides," Journal of the American Chemical Society (1954); vol. 76, pp. 1926-1929.

* cited by examiner

Primary Examiner — Golam M M Shameem
Assistant Examiner — Karen Cheng
(74) Attorney, Agent, or Firm — Fox Rothschild LLP; Peter J. Butch, III; Wansheng Jerry Liu

(57) ABSTRACT

There is provided a means to produce industrially a highly pure 2-hydroxy-4-oxa-5-thiatricyclo[4.2.1.0$^{3,7}$]nonane 5,5-dioxide derivative in high yield from highly pure and industrially available raw materials.

The production method for a sultone derivative of the present invention comprises a step (A) to obtain a sulfonic acid derivative by hydrolyzing a sulfonyl halide derivative represented by the following chemical formula 1:

[Chemical Formula 1]

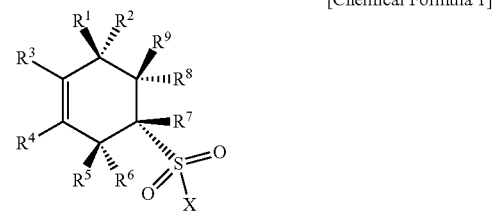

or an enantiomer thereof and a step (B) to obtain a corresponding sultone derivative represented by the following chemical formula 2:

[Chemical Formula 2]

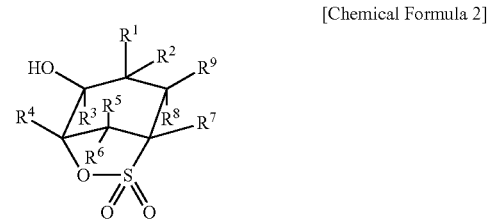

or an enantiomer thereof by treating the sulfonic acid derivative with a oxidizing agent.

7 Claims, No Drawings

PRODUCTION METHOD FOR SULTONE DERIVATIVES

CROSS REFERENCE TO RELATED APPLICATIONS

The present application is a 35 U.S.C. §371 National Phase application of International Application Serial No. PCT/JP09/065,290, filed Sep. 2, 2009, which claims priority to Japanese Application Serial No. 2008-224632, filed Sep. 2, 2008. The disclosures of both applications are incorporated herein by reference in their entireties.

TECHNICAL FIELD

The present invention relates to a production method for sultone derivatives. The sultone derivatives obtainable by the present invention are useful as raw materials of paints and functional polymers as well as raw materials of fine chemical products of medicines, agricultural chemicals, and the like.

BACKGROUND ART

Sultone compound which is an intramolecular cyclic ester of a hydroxysulfonic acid has a —$SO_2$—O— group as a part of the ring. Among such sultone compounds, as the one in which a plurality of rings are present in a molecule, for example, 4-hydroxy-6-oxa-7-thiabicyclo[3.2.1]octane 7,7-dioxide derivative (in the present description, this derivative is also simply referred to as "sultone derivative") represented by the following chemical formula 3 or an enantiomer thereof is known. It should be noted that the following chemical formula 3 shows locants in a bicyclooctane ring.

[Chemical Formula 3]

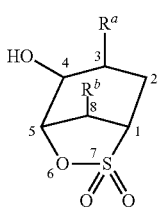

As such a sultone derivative, for example, 2-hydroxy-4-oxa-5-thiatricyclo[4.2.1.0$^{3,7}$]nonane 5,5-dioxide derivative represented by the chemical formula 4, which has a norbornane skeleton in which $R^a$ and $R^b$ in chemical formula 3 are bound together to form a methylene group, is known. It should be noted that the following chemical formula 4 shows locants in a tricyclononane ring.

[Chemical Formula 4]

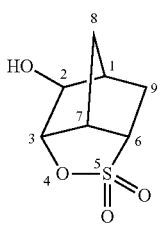

And as a technology to produce such 2-hydroxy-4-oxa-5-thiatricyclo[4.2.1.0$^{3,7}$]nonane 5,5-dioxide derivative, several methods have been proposed. For example, as shown in the following reaction scheme 1, method (1) to obtain a sultone derivative having a norbornane skeleton has been proposed. That is, Diels-Alder reaction of cyclopentadiene (CPD) and vinyl thioacetate is carried out to prepare 2-acetylthio-5-norbornene; and said norbornene derivative is oxidized using a peracid (peracetic acid) to be converted to methyl 5-norbornene-2-sulfonate, which is an ester of sulfonic acid; subsequently the double bond is epoxidized; and then methyl sulfonate group is hydrolyzed and cyclized in the presence of an acid (see Non-Patent Literature 1).

[Reaction Scheme 1]

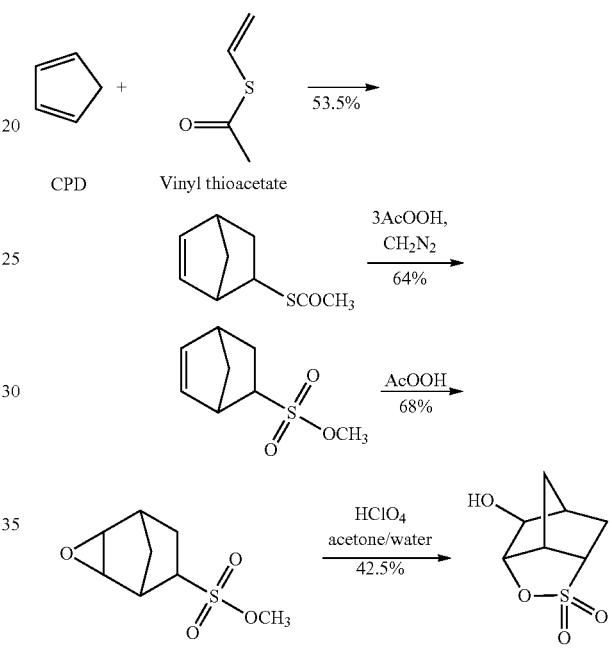

In addition, as shown in the following reaction scheme 2, method (2) to obtain a sultone derivative having a norbornane skeleton has been proposed. That is, Diels-Alder reaction of cyclopentadiene and methyl vinylsulfonate is carried out to prepare a sulfonate ester (methyl 5-norbornene-2-sulfonate); and the double bond thereof is epoxidized; subseguentlymethyl sulfonate group is hydrolyzed with an alkali; then the sulfonic acid is subjected to acid treatment to be cyclized (see Patent Literature 1).

[Reaction Scheme 2]

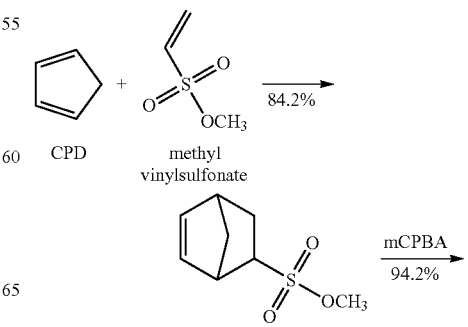

-continued

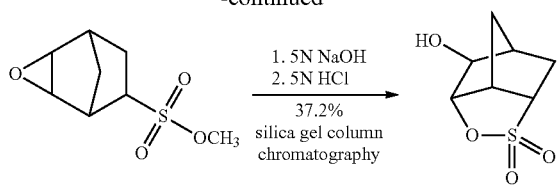

LITERATURES FOR PRIOR ART

Patent Literatures

Patent Literature 1: JP-A-2007-31355

Non-Patent Literatures

Non-Patent Literature 1: Zhurnal Organicheskoi Khimii, 2 (11), 1954-1961 (1966) (in particular, lower part of page 1957)

SUMMARY OF INVENTION

Problem to be Solved by the Invention

Here, in method (1) described above, as mentioned above referring to reaction scheme 1, it is necessary to use vinyl thioacetate as a raw material. However, it is difficult to procure vinyl thioacetate industrially. Further, yield of 2-hydroxy-4-oxa-5-thiatricyclo[4.2.1.0$^{3,7}$]nonane 5,5-dioxide from 2-acetylthio-5-norbornene is less than 20%, and therefore it is hard to say that this method is a satisfactory one.

In addition, in method (2) described above, as mentioned above referring to reaction scheme 2, it is necessary to use methyl vinylsulfonate as a raw material. However, there is a problem that methyl vinylsulfonate is also difficult to procure industrially similarly to vinyl thioacetate. It should be noted that, in method (2), yield in the epoxidation step for the double bond of methyl 5-norbornene-2-sulfonate is as high as about 94%. However, yield of the subsequent hydrolysis and cyclization step of the methyl sulfonate group is as low as about 37%, and due to this, yield from methyl 5-norbornene-2-sulfonate is also reduced to about 35%. Further, since the purification method for sultone derivative specifically disclosed in Patent Literature 1 is only silica gel column chromatography, there is a room for improvement as an industrial production method.

Therefore, it is an object of the present invention to provide a means to produce industrially a highly pure sultone derivative in high yield from highly pure and industrially available raw materials.

Means for Solving the Problem

The inventors of the present invention have intensively studied to solve the problem described in the above Background Art, and as a result, surprisingly have found that in synthesis of sultone derivative, the above-described various problems can be solved by a method in which a predetermined compound (sulfonyl halide derivative) having a sulfonyl halide group is hydrolyzed to a sulfonic acid derivative, which is then treated with an oxidizing agent, and have accomplished the present invention.

That is, the production method for a sultone derivative of the present invention comprises:

a step (A) to obtain a sulfonic acid derivative by hydrolyzing a sulfonyl halide derivative represented by the following chemical formula 1:

[Chemical Formula 1]

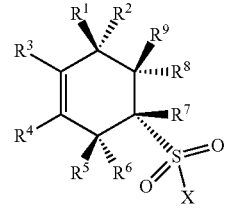

or an enantiomer thereof, and a step (B) to obtain a corresponding sultone derivative represented by the following chemical formula 2:

[Chemical Formula 2]

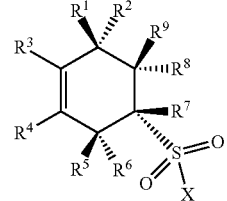

or an enantiomer thereof by treating the sulfonic acid derivative with an oxidizing agent.

Effects of the Invention

According to the present invention, it is possible to produce industrially a highly pure sultone derivative in high yield from highly pure and industrially available raw materials.

MODE FOR CARRYING OUT THE INVENTION

The production method for sultone derivatives of the present invention is generally stated as follows. That is, the method comprises Step (A) to obtain a sulfonic acid derivative by hydrolyzing a sulfonyl halide derivative represented by the following chemical formula 1:

[Chemical Formula 1]

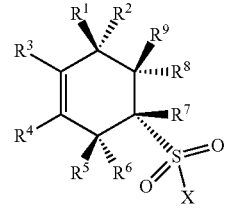

or an enantiomer thereof, and Step (B) to obtain a corresponding sultone derivative represented by the following chemical formula 2:

[Chemical Formula 2]

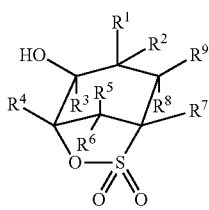

or an enantiomer thereof by treating the sulfonic acid derivative with an oxidizing agent. Thus, the production method of the present invention is different from the technologies described in Non-Patent Literature 1 and Patent Literature 1 in which methyl 5-norbornene-2-sulfonate is oxidized (epoxidized) before hydrolysis step is carried out, in a point that sulfonyl halide derivative is hydrolyzed before oxidation (epoxidation and cyclization) is carried out.

Hereinafter, the embodiment for carrying out the present invention will be explained in detail in the order of the steps.

[Step (A)]

In step (A), a sulfonyl halide derivative represented by the chemical formula 1 or an enantiomer thereof is hydrolyzed. By this hydrolysis, a sulfonic acid derivative can be obtained.

(Raw Materials)

In step (A), firstly a sulfonyl halide represented by the following chemical formula 1 or an enantiomer thereof is arranged as a raw material of the reaction.

[Chemical Formula 1]

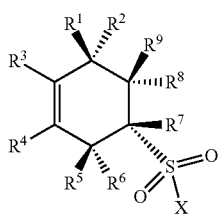

In chemical formula 1, $R^1$ to $R^9$ represent each independently a hydrogen atom, an alkyl group having 1 to 10 carbon atoms, a cycloalkyl group having 3 to 10 carbon atoms or an alkoxy group having 1 to 10 carbon atoms.

Here, the alkyl group having 1 to 10 carbon atoms may be any of linear or branched, and an example thereof includes, for example, methyl group, ethyl group, n-propyl group, isopropyl group, n-butyl group, isobutyl group, sec-butyl group, tert-butyl group, n-pentyl group, isopentyl group, n-hexyl group, n-heptyl group, n-octyl group, n-nonyl group, n-decanyl group, and the like. In addition, the cycloalkyl group having 3 to 10 carbon atoms includes, for example, cyclopropyl group, cyclobutyl group, cyclopentyl group, cyclohexyl group, cycloheptyl group, cyclooctyl group, cyclononyl group, cyclodecanyl group, norbornanyl group, adamantyl group, and the like. Further, the alkoxy group having 1 to 10 carbon atoms includes, for example, methoxy group, ethoxy group, n-propoxy group, isopropoxy group, n-butoxy group, isobutoxy group, sec-butoxy group, tert-butoxy group, n-pentyloxy group, isopentyloxy group, n-hexyloxy group, n-heptyloxy group, n-octyloxy group, n-nonyloxy group, n-decanyloxy group, and the like.

In addition, optionally, $R^1$ and $R^5$ may be bound together. In this case, $R^1$ and $R^5$ form together an alkylene group having 1 to 6 carbon atoms which may contain an oxygen atom or a sulfur atom in an arbitrary position, —O—, or —S—. Here, the alkylene group having 1 to 6 carbon atoms includes methylene group, ethylene group, trimethylene group, propylene group, methylmethylene group, dimethylmethylene group, ethylmethylene group, ethylmethylmethylene group, tetramethylene group, ethylethylene group, pentamethylene group, hexamethylene group, cyclohexylene group, and the like.

In a preferable embodiment, $R^1$ and $R^5$ represent each independently a hydrogen atom, a methyl group or an ethyl group, or form together a methylene group, —O—, or —S—. More preferably $R^1$ and $R^5$ are bound together to form a methylene group, —O, or —S—, and further more preferably form a methylene group. It should be noted that, when $R^1$ and $R^5$ are bound together to form a methylene group, the compound represented by the chemical formula 1 has a norbornene skeleton. Similarly, when $R^1$ and $R^5$ are bound together to form —O— or —S—, the compound represented by chemical formula 1 has an oxanorbornene sleleton or a thianorbornene sleleton, respectively.

In a preferable embodiment, $R^2$ to $R^4$ and $R^6$ to $R^9$ represent each independently a hydrogen atom, a methyl group or an ethyl group, more preferably a hydrogen atom or a methyl group, and particularly preferably a hydrogen atom.

In chemical formula 1, X represents a fluorine atom, a chlorine atom, or a bromine atom, preferably a fluorine atom or a chlorine atom, and particularly preferably a chlorine atom.

An example of the sulfonyl halide derivative represented by chemical formula 1 includes, for example 5-norbornene-2-sulfonyl chloride, 7-oxa-5-norbornene-2-sulfonyl chloride and 7-thia-5-norbornene-2-sulfonyl chloride represented by the following chemical formulas 5 to 7, respectively, as well as 3-cyclohexene-1-sulfonyl chloride, bicyclo[2.2.2]oct-5-ene-2-sulfonyl chloride, and the like.

[Chemical Formula 5]

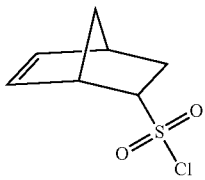

[Chemical Formula 6]

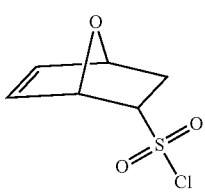

[Chemical Formula 7]

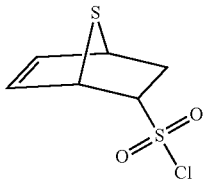

The sulfonyl halide derivative to be arranged as a raw material may be optically active or optically inactive (racemic form). As for procurement of said derivative, when a commercial product is available, said derivative can be arranged by purchasing the commercial product. Alternatively, said derivative may be arranged by preparing per se. Method to prepare personally a sulfonyl halide derivative is not particularly limited, and heretofore known knowledge in the technical field of the organic chemistry can be properly referred to.

Briefly speaking, the sulfonyl halide derivative can be obtained by carrying out a Diels-Alder reaction of a diene derivative and a vinylsulfonyl halide. And the vinylsulfonyl halide can be obtained, for example, by a dehydrohalogenation reaction of a dihalide having a structure in which hydrogen halide is added to the double bond of said vinylsulfonyl halide. According to such embodiment, the sulfonyl halide derivative can be produced from an industrially available diene derivative and a dihalide. Hereinafter, such method will be explained in detail.

Firstly, as one of raw materials, a diene derivative represented by the following chemical formula 8 is arranged.

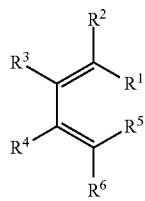

[Chemical Formula 8]

In chemical formula 8, $R^1$ to $R^6$ have each the same definitions as in the above-described chemical formula 1. Specific embodiments of these substituents can be selected depending on the sulfonyl halide derivative to be obtained, eventually the desired structure of sultone derivative which is the final product of the production method of the present invention. A specific example of the diene derivative represented by the chemical formula 8 includes chain-like conjugated diene such as butadiene, isoprene, 1,3-pentadiene, 1,3-hexadiene, 2,4-hexadiene, 2,3-dimethylbutadiene; cyclopentadiene derivative such as 1,3-cyclopentadiene, 1-methyl-1,3-cyclopentadiene, 2-methyl-1,3-cyclopentadiene, 5-methyl-1,3-cyclopentadiene, 1,2-dimethyl-1,3-cyclopentadiene, 1,4-dimethyl-1,3-cyclopentadiene, 2,3-dimethyl-1,3-cyclopentadiene, 1,2,3,4-tetramethyl-1,3-cyclopentadiene, 1,2,3,4,5-pentamethyl-1,3-cyclopentadiene; furan derivative such as furan, 2-methylfuran, 3-methylfuran, 2,5-dimethylfuran, 3,4-dimethylfuran, 2,3,4,5-tetramethylfuran; and thiophene derivative such as thiophene, 2-methylthiophene, 3-methylthiophene, 2,5-dimethylthiophene, 3,4-dimethylthiophene, 2,3,4,5-tetramethylthiophene.

On the other hand, as another raw material, a dihalide represented by the following chemical formula 9 is arranged.

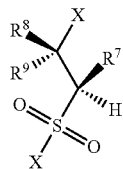

[Chemical Formula 9]

In chemical formula 9, $R^7$ to $R^9$ and X have each the same definitions as in the above-described chemical formula 1. In addition, two Xs in chemical formula 9 may be same or different from each other, but is preferably same each other. Further, X bound to sulfur atom can be selected depending on the desired structure of sulfonyl halide derivative to be obtained. A specific example of the dihalide represented by chemical formula 9 includes 2-chloroethanesulfonyl chloride, 2-bromoethanesulfonyl chloride, 2-fluoroethanesulfonyl chloride, 2-bromoethanesulfonyl bromide, 2-fluoroethanesulfonyl bromide, 2-chloroethanesulfonyl bromide, 2-fluoroethanesulfonyl fluoride, 2-chloroethanesulfonyl fluoride, 2-bromoethanesulfonyl fluoride, 2-chloropropane-1-sulfonyl chloride, 1-chloropropane-2-sulfonyl chloride, 2-chlorobutane-1-sulfonyl chloride, 1-chlorobutane-2-sulfonyl chloride, and the like.

It should be noted that, in chemical formula 9, when $R^7$ is not a hydrogen atom or $R^8$ and $R^9$ are different from each other, a dihalide which is an enantiomer of the compound represented by chemical formula 9 may be used as a raw material in this step.

Subsequently, the dihalide arranged as mentioned above is subjected to a dehydrohalogenation reaction. By this reaction, hydrogen halide is 1,2-eliminated, to give a vinylsulfonyl halide represented by chemical formula 10.

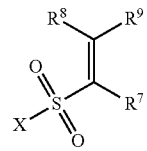

[Chemical Formula 10]

In chemical formula 10, $R^7$ to $R^9$ and X have each the same definitions as in the above-described chemical formula 1. A specific example of the vinylsulfonyl halide represented by chemical formula 10 includes, for example, vinylsulfonyl chloride ($CH_2$=$CH$—$SO_2Cl$), vinylsulfonyl bromide ($CH_2$=$CH$—$SO_2Br$), and vinylsulfonyl fluoride ($CH_2$=$CH$—$SO_2F$), in which all of R' to $R^9$ are a hydrogen atom.

Specific embodiment of the dehydrohalogenation reaction of the dihalide represented by chemical formula 9 is not particularly limited, and heretofore known knowledge can be properly referred to. For example, by carrying out a reaction of the diene derivative (chemical formula 8) and the dihalide (chemical formula 9) in the presence of a base, 1,2-elimination of hydrogen halide from the above-described dihalide proceeds, to give the vinylsulfonyl halide (chemical formula 10).

Amount of the diene derivative (chemical formula 8) to be used in this step is preferably in a range of 0.8 to 50 moles, more preferably in a range of 0.9 to 20 moles, and further more preferably in a range of 1.0 to 10 moles relative to 1 mole of the dihalide (chemical formula 9).

The base to be used in this step includes alkali metal hydride such as sodium hydride and potassium hydride; alkaline earth metal hydride such as magnesium hydride and calcium hydride; alkali metal hydroxide such as sodium hydroxide and potassium hydroxide; alkaline earth metal hydroxide such as magnesium hydroxide and calcium hydroxide; carbonate salt of alkali metal such as sodium carbonate and potassium carbonate; carbonate salt of alkaline earth metal such as magnesium carbonate and calcium carbonate; hydrogen carbonate salt of alkali metal such as sodium hydrogen carbonate and potassium hydrogen carbonate; alkaline earth metal oxide such as magnesium oxide and calcium oxide; tertiary amine such as triethylamine, tributylamine and diisopropylethylamine; and nitrogen-containing aromatic cyclic compound such as pyridine, 2-methylpyridine, 2,6-dimethylpyridine, collidine and quinoline.

Amount of the base to be used in this step is preferably in a range of 0.8 to 5 moles, and more preferably in a range of 0.8 to 3 moles, relative to 1 mole of the dihalide (chemical formula 9) from the viewpoint of economic efficiency and easiness of post-treatment.

This step can be carried out in the presence of or in the absence of a polymerization inhibitor. The polymerization inhibitor includes, for example, besides phenothiazine, quinones such as p-benzoquinone, p-naphthoquinone and 2,5-diphenyl-p-benzoquinone; hydroquinones such as hydroquinone, hydroquinone monomethyl ether, hydroquinone monoethyl ether, hydroquinone monobutyl ether and mono-tert-butylhydroquinone; and phenols such as di-tert-butyl-p-cresol and naphthol. Among them, phenothiazine is preferably used. The polymerization inhibitor may be used alone or in combination of two or more kinds. When the polymerization inhibitor is used, amount thereof to be used is preferably 5% by mass or less, more preferably 1% by mass or less, and further more preferably 0.5% by mass or less, relative to the mass of the whole reaction mixture. The amount is usually 10 to 10,000 ppm by mass.

This step can be carried out in the presence of or in the absence of a solvent. The solvent is not particularly limited so long as it does not inhibit the reaction. The solvent includes, for example, aliphatic hydrocarbon such as hexane, heptane and octane; aromatic hydrocarbon such as benzene, toluene, xylene and mesitylene; halogenated aromatic hydrocarbon such as chlorobenzene and fluorobenzene; ether such as diethyl ether, dipropyl ether, dibutyl ether, tetrahydrofuran, dioxane, 1,2-dimethoxyethane, diglyme, triglyme and tetraglyme; halogenated aliphatic hydrocarbon such as dichloromethane, chloroform and 1,2-dichloroethane; and acetonitrile; and the like. These solvents may be used alone or in combination of two or more kinds. When a solvent is used, amount thereof to be used is preferably 100 parts by mass or less, more preferably 50 parts by mass or less, and further more preferably 10 parts by mass or less relative to 1 part by mass of the dihalide (chemical formula 9), from the viewpoints of reaction rate, economic efficiency, environmental conservation, and the like.

Reaction temperature of this step varies depending on kinds of diene derivative (chemical formula 8), dihalide (chemical formula 9) and base to be used, but the temperature is usually in a range of −30° C. to 200° C. From the viewpoint of reaction rate, the reaction temperature is preferably −20° C. or higher, and more preferably −10° C. or higher. In addition, from the viewpoint of inhibition of side reaction such as polymerization, the reaction temperature is preferably 100° C. or lower, and more preferably 50° C. or lower.

Reaction pressure of this step is not particularly limited, but preferably the reaction is carried out under ordinary pressure because of easiness and simplicity.

Reaction time of this step varies depending on kinds of diene derivative (chemical formula 8), dihalide (chemical formula 9), base and reaction temperature to be used, but the reaction time is usually preferably in a range of 0.5 hour to 48 hours, and more preferably in a range of 1 hour to 24 hours.

Operation procedure of reaction in this step is not particularly limited, so long as the reaction is carried out in a state in which diene derivative (chemical formula 8), dihalide (chemical formula 9) and base are present together in a reactor. The operation procedure of reaction includes, for example, (1) a method in which reaction is carried out by charging a dihalide, a diene derivative, a base, a polymerization inhibitor if necessary, and optionally a solvent in a batch-wise reactor, (2) a method in which a diene derivative, a base, a polymerization inhibitor if necessary, and optionally a solvent are charged in a batch-wise reactor, then a dihalide is added to this mixture at the prescribed temperature, (3) a method in which a diene derivative, a dihalide, a polymerization inhibitor if necessary, and optionally a solvent are charged in a batch-wise reactor, then a base is added to this mixture at the prescribed temperature, (4) a method in which a diene derivative, a polymerization inhibitor if necessary, and optionally a solvent are charged in a batch-wise reactor, then a dihalide and a base are added separately to this mixture at the prescribed temperature, and the like, and the methods of (3) and (4) are preferable.

In this step, by reacting the above-described dihalide and diene derivative, the sulfonyl halide derivative represented by chemical formula 1 or an enantiomer thereof can be obtained.

The reaction mixture obtained in this step can be used for other reaction as it is, or can be isolated and purified. Method for isolation and purification can be carried out by the method which is generally used for isolation and purification of organic compounds. For example, a sulfonyl halide derivative (chemical formula 11) can be isolated by filtering reaction mixture after completion of the reaction, and then concentrating the resultant filtrate. And, if necessary, by purifying by recrystallization, distillation, silica gel column chromatography, or the like, a highly pure sulfonyl halide derivative (chemical formula 11) can be also obtained.

By the step mentioned above, sulfonyl halide derivative can be obtained from diene derivative and dihalide. That is, according to other embodiment of the present invention, the production method for sulfonyl halide derivatives comprising a step to obtain a sulfonyl halide derivative (or an enantiomer thereof) represented by chemical formula 1 by carrying out Diels-Alder reaction of a diene derivative represented by chemical formula 8 and a vinylsulfonyl halide represented by the following chemical formula 10 which is obtained by dehydrohalogenation reaction of a dihalide represented by chemical formula 9, can also be provided.

(Hydrolysis)

In step (A), the sulfonyl halide derivative prepared as described above is hydrolyzed. By this hydrolysis, sulfonic acid derivative can be obtained. Specifically, a sulfonyl halide group contained in the sulfonyl halide derivative is hydrolyzed to form a sulfonic acid group.

Specific embodiment of the hydrolysis is not particularly limited, and heretofore known technology which is capable of hydrolyzing a sulfonyl halide group to form a sulfonic acid group can be properly employed. In a preferable embodiment, hydrolysis of a sulfonyl halide derivative represented by chemical formula 1 is carried out in the presence of a base. Hereinafter, such preferable embodiment will be explained in detail, however, technical scope of the present invention is not limited only to such embodiment. Optionally, other means (for example, hydrolysis in the presence of acid, or hydrolysis in the absence of acid or base) may be employed.

The base to be used in the hydrolysis of sulfonyl halide derivative is not particularly limited, and may be an inorganic base or an organic base. An example of the inorganic base includes, for example, sodium hydroxide, sodium carbonate, sodium hydrogen carbonate, potassium hydroxide, potassium carbonate, potassium hydrogen carbonate, and the like. In addition, an example of the organic base includes, for example, nitrogen-containing organic base such as tertiary amine and nitrogen-containing aromatic compound. Optionally, phosphorus-containing organic base such as phosphazene base and proazaphosphatrane base may be used. Here, tertiary amine includes, for example, chain-like aliphatic tertiary amine such as trimethylamine, triethylamine, tripropylamine, tributylamine and diisopropylethylamine; cyclic aliphatic tertiary amine such as N-methylpyrrolidine, N-methylpiperidine, N-methylmorpholine, 1,4-diazabicyclo[2.2.2]octane, 1,5-diazabicyclo[4.3.0]nonan-5-ene and 1,8-diazabicyclo[5.4.0]undec-7-ene; and aromatic tertiary amine such as N,N-dimethylaniline. In addition, nitrogen-containing aromatic compound includes, for example, pyrrole derivative such as pyrrole and N-methylpyrrole; imidazole derivative such as imidazole, 1-methylimidazole, 2-methylimidazole and 4-methylimidazole; triazole; pyridine derivative such as pyridine, 4-(dimethylamino)pyridine, 2-methylpyridine, 3-methylpyridine, 4-methylpyridine, 2,4-dimethylpyridine, 2,6-dimethylpyridine, 3,4-dimethylpyridine, 3,5-dimethylpyridine, 2-methoxypyridine, 2-cyanopyridine, 3-cyanopyridine, 4-cyanopyridine, bipyridyl, collidine, quinoline and isoquinoline; pyridazine derivative such as pyridazine, 3-methylpyridazine and 4-methylpyridazine; pyrimidine derivative such as pyrimidine and 4-methylpyrimidine; pyrazine derivative such as pyrazine and 2-methylpyrazine; triazine; and the like.

In a preferable embodiment, from the viewpoint of prevention of decrease in endo/exo ratio in sulfonyl halide derivative and prevention of purity deterioration of the final product accompanying thereto, the base is an organic base, more preferably a nitrogen-containing organic base, further more preferably a nitrogen-containing aromatic compound, particularly preferably an imidazole derivative or a pyridine derivative, and most preferably pyridine (see Example 2 to be described later). It should be noted that, the above-described base may be used alone or in combination of two or more kinds.

In this step (A), amount of the base to be used in the hydrolysis of sulfonyl halide derivative is not particularly limited. As one example, the amount of the base to be used is preferably 1 to 10 moles, and more preferably 1 to 5 moles relative to 1 mole of the sulfonyl halide derivative to be hydrolyzed. In addition, amount of water to be used for the hydrolysis may be such an amount that when a sulfonyl halide group of the sulfonyl halide derivative is hydrolyzed to form a salt, this salt can dissolve to form an aqueous solution, and is preferably roughly 1 to 10 parts by mass relative to 1 part by mass of the sulfonyl halide derivative.

Reaction temperature when the hydrolysis is carried out varies depending on kind and amount of the base to be used, as well as amount of water to be used, but is preferably roughly in a range of 0 to 100° C.

Embodiment of hydrolyzing the sulfonyl halide derivative in the presence of a base is not particularly limited, so long as the sulfonyl halide derivative can be present together with water and the base. For example, an embodiment in which the sulfonyl halide derivative is added to an aqueous alkali solution containing a base, an embodiment in which both of the sulfonyl halide derivative and a base are added dropwise to water, and the like can be employed.

It should be noted that, when the sulfonyl halide derivative is hydrolyzed in the presence of a base, the product is generally present in the reaction system as a sulfonate salt (for example, sodium salt). In the present invention, such sulfonate salt is also included in the concept of the "sulfonic acid derivative".

[Step (B)]

In step (B), the sulfonic acid derivative obtained in the above-described step (A) is treated with an oxidizing agent. By this treatment, a corresponding sultone derivative represented by the following chemical formula 2 or an enantiomer thereof (final product) is obtained.

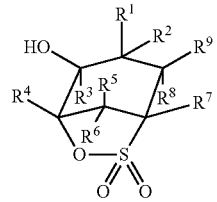

[Chemical Formula 2]

In chemical formula 2, $R^1$ to $R^9$ have each the same definitions as in the above-described chemical formula 1.

In step (B), specific embodiment of treating the sulfonic acid derivative with an oxidizing agent is not particularly limited, and heretofore known knowledge can be properly referred to.

The oxidizing agent which can be used in step (B) includes, for example, peracid and peroxide. Peracid includes, for example, organic peracid like percarboxylic acid such as performic acid, peracetic acid, trifluoroperacetic acid, perbenzoic acid, m-chlorobenzoic acid and monoperoxiphthalic acid; inorganic peracid such as permanganic acid; and salts thereof. It should be noted that, when an organic peracid is used as a peracid, said organic peracid may be equilibrium peracid such as equilibrium performic acid and equilibrium peracetic acid. When the equilibrium peracid is used, for example, an acid (for example, formic acid and acetic acid) corresponding to the desired peracid and hydrogen peroxide may be added in combination to the reaction system. By this procedure, the desired organic peracid is formed in the reaction system.

Peroxide includes, for example, hydrogen peroxide, peroxide and hydroperoxide, as well as peroxoacid and salt thereof, and the like. Hydrogen peroxide may be used in a form of pure hydrogen peroxide ($H_2O_2$), but is usually used in a diluted form (for example, an aqueous 30% by weight hydrogen peroxide solution) with a suitable solvent (e.g. water) from the viewpoint of easiness in handling.

It should be noted that, when hydrogen peroxide is used as a peroxide, a metal compound is often used in combination. As for specific embodiment (kind and amount of a metal compound to be used) when a metal compound is used in combination with hydrogen peroxide, the description of the paragraphs "0036" to "0041" in the above-described Patent Literature 1 (JP-A-2007-31355) can be properly referred to.

Among the oxidizing agents, preferably an organic peracid is used, more preferably an equilibrium peracid is used, particularly preferably performic acid or peracetic acid which can be obtained as an equilibrium peracid, and most preferably performic acid which can be obtained as an equilibrium peracid is used.

Amount of the oxidizing agent to be used for the treatment of sulfonic acid derivative is also not particularly limited, but is usually around 0.5 to 10 moles, and preferably around 0.8 to 3 moles relative to 1 mole of sulfonic acid derivative from the viewpoints of economic efficiency and easiness of post-treatment.

The treatment of sulfonic acid derivative with an oxidizing agent (for example, a peracid or a peroxide) may be carried out in the presence of a solvent or in the absence of a solvent, but preferably carried out in the presence of a solvent. The solvent which can be used in step (B) is not particularly limited so long as the solvent does not inhibit the reaction, but includes, for example, water; aliphatic hydrocarbon such as hexane, heptane and octane; aromatic hydrocarbon such as toluene, xylene and cymene; halogenated hydrocarbon such as methylene chloride and dichloroethane; ether such as tetrahydrofuran and diisopropyl ether; and carboxylic acid such as formic acid and acetic acid. Amount of the solvent when it is used is preferably 0.1 to 20 parts by mass, and more preferably 0.3 to 10 parts by mass relative to 1 part by mass of sulfonyl halide derivative, from the viewpoint of economic efficiency and easiness of post-treatment. It should be noted that, these solvents may be used alone or in combination of two or more kinds. In addition, when an equilibrium peracid is used as an oxidizing agent, preferably the solvent contains water, and most preferably water is used alone as a solvent, from the viewpoints of reaction rate and yield.

Temperature of the reaction system when sulfonic acid derivative is treated with an oxidizing agent is not particularly limited, and can be properly decided considering desired reaction rate and reaction selectivity, as well as kind of oxidizing agent. However, the temperature is usually around −40 to 100° C., and preferably around 10 to 80° C. It should be noted that, the reaction can be carried out in any type of batch type, semi-batch type, continuous type, and the like.

The oxidation reaction with an oxidizing agent in step (B) can be terminated by adding a reducing agent. The reducing agent to be used is not particularly limited, but includes, for example, sulfite salt such as sodium sulfite and sodium hydrogen sulfite; sulfide such as dimethylsulfide and diphenylsulfide; and the like. It should be noted that, amount of the reducing agent to be used is also not particularly limited, but is preferably in a range of 1.0 to 5.0 equivalents relative to an exceeding amount of oxidizing agent.

In step (B), a sultone derivative which is the final product can be obtained by treating a sulfonic acid derivative with an oxidizing agent as described above, and a mechanism of this reaction can be understood as follows. That is, by the treatment with an oxidizing agent, firstly the double bond of the sulfonic acid derivative is epoxidized to form an epoxide as a reaction intermediate. Subsequently, the oxygen atom binding by a single bond to a sulfur atom in the sulfonic acid group binding in the endo position attacks neucleophilically the side closer to oxygen atom among the carbon atoms in the root of the epoxide group resulting intramolecular cyclization together with ring-opening of the epoxide ring. It should be noted that, pH of the reaction system may be adjusted at around neutral by adding a base to the reaction system if necessary. Finally, the sultone derivative, in which a hydroxyl group is bound at an exo position as represented by chemical formula 2, can be obtained.

The sultone derivative obtained as the final product can be isolated and purified by a separation means such as, for example, filtration, concentration, distillation, extraction, crystallization, recrystallization, column chromatography, and the like, or by combining these means.

According to the production method of the present invention, by producing a sultone derivative via the above-described steps (A) and (B), it is possible to produce a highly pure sultone derivative in higher yield in comparison with the conventional art as described later. This reason has not been completely clarified yet, but the following mechanism has been supposed. That is, in the conventional method, intramolecular cyclization is progressed by the hydrolysis of sulfonate ester, whereas in the method of the present invention, sulfonyl chloride which has comparatively high reactivity is used as a target of the hydrolysis reaction. For this reason, it is considered that the hydrolysis reaction proceeds under a comparatively mild condition and in a short time and progression of side reaction can be inhibited. In addition, in the conventional method, the epoxide ring itself can receive the hydrolysis because the epoxy compound is subjected to the hydrolysis reaction, whereas the production method of the present invention does not have such fear. For this reason, it is presumed that decrease in purity might be inhibited.

In addition, according to the production method of the present invention, a sultone derivative which is the final product can be recovered by such a simple and easy method as crystallization method, as similarly shown in Examples to be described later. The recovery by the crystallization method of the sultone derivative produced by the heretofore known method was tried, however, recovery by such crystallization method was impossible as described in Comparative Example to be described later. Although this cause has not been completely clarified yet, it is presumed as follows. That is, by the conventional method, crystallized product cannot be obtained due to low purity of the crude product (sultone derivative), whereas by the production method of the present invention, purity of crude product becomes high, and as a result, recovery by the crystallization method might become possible. It should be noted that, the above description on the mechanism of working effect of the present invention is only based on presumption. Therefore, even if the above-described working effect were obtained actually by a different mechanism, technical scope of the present invention is not affected in any way.

The sultone derivative produced by the production method of the present invention can be suitably used as a raw material for paints and functional polymers, or a raw material for fine chemicals such as medicines, agricultural chemicals and the like, optionally in a form of ester with (meth)acrylic acid as described in Patent Literature 1 (JP-A-2007-31355).

EXAMPLES

Hereinafter, the effects of the present invention will be explained in more detail by Examples and Comparative Examples, however, technical scope of the present invention is not limited only to the following Examples.

Example 1

Synthesis of 5-norbornene-2-sulfonyl chloride

Into a four-necked flask having an inner volume of 3 L equipped with a stirrer and a thermometer, phenothiazine (0.40 g), tetrahydrofuran (THF, 1154 g), cyclopentadiene (87.0 g, 1.32 mol) were charged, and cooled down to 5° C. or lower with stirring. Subsequently, 2-chloroethanesulfonyl chloride (195.7 g, 1.20 mol) and triethylamine (146.0 g, 1.45 mol) were each weighed into separate dropping funnels, and simultaneously dropping was carried out at the inner temperature of 5 to 10° C. over 3 hours. After completion of the dropping, the reaction mixture was stirred at 5 to 10° C. for 3 hours, then the precipitated salt was filtered under the reduced pressure, followed by rinsing the filtered out salt with THF (600.0 g), to obtain a filtrate (1633 g) (this filtrate is also referred to as "Filtrate A"). Filtrate A was analyzed by a gas chromatography to confirm that 5-norbornene-2-sulfonyl chloride (178.2 g, 0.925 mol) was contained. It should be noted that, yield of 5-norbornene-2-sulfonyl chloride from 2-chloroethanesulfonyl chloride was 77.1%. In addition, endo/exo ratio of 5-norbornene-2-sulfonyl chloride contained in Filtrate A was 90/10.

Example 2

Synthesis of 2-hydroxy-4-oxa-5-thiatricyclo[4.2.1. $0^{3,7}$]nonane 5,5-dioxide using sodium hydroxide as a base Into a three-necked flask having an inner volume of 3 L equipped with a stirrer, a thermometer and a dropping funnel, water (920 g) was poured, and cooled down to 20° C. or lower. Sodium hydroxide (80.3 g, 2.01 mol) was added thereto with stirring so that the inner temperature was maintained at 20° C. or lower. "Filtrate A" (1300 g) (contains 5-norbornene-2-sulfonyl chloride (endo/exo ratio=90/10) (141.9 g, 0.737 mol), which was obtained in the above-described Example 1, was weighed into a dropping funnel, and this filtrate was added dropwise to the reaction system over 4 hours so that the inner temperature of the reaction system was maintained in a range of 20 to 25° C. After 1 hour from completion of the dropping, the reaction liquid was analyzed by gas chromatography to confirm that 5-norbornene-2-sulfonyl chloride was completely disappeared. The reaction liquid was concentrated under the reduced pressure to remove THF. After that, the reaction liquid was transferred to a separating funnel of 2 L, washed with toluene (300 g) 3 times, to obtain an aqueous solution (1065 g) containing sodium 5-norbornene-2-sulfonate (this aqueous solution is also referred to as "Aqueous Solution A"). It should be noted that, endo/exo ratio of sodium 5-norbornene-2-sulfonate contained in Aqueous Solution A was 55/45.

Into a three-necked flask having an inner volume of 3 L equipped with a stirrer, a thermometer and a dropping funnel, the whole amount of "Aqueous Solution A" obtained above was poured, and cooled down to 10° C. 99% Formic acid (93.27 g, 2.01 mol) was weighed into a dropping funnel, and added dropwise to the reaction system so that the inner temperature of the reaction system was maintained in a range of 11 to 15° C. After that, the inner temperature was raised up to 50 to 53° C. by heating, and then 30% hydrogen peroxide aqueous solution (162.50 g, 1.43 mol) weighed and contained in another dropping funnel was added dropwise to the reaction system over 3 hours. It should be noted that, after completion of the dropping, the inner temperature of the reaction system was also maintained at around 50° C. After 17 hours from completion of the dropping, the reaction liquid was analyzed by HPLC to confirm that conversion ratio of sodium 5-bornene-2-sulfonate was 98.7%. After cooling down the reaction liquid to 15° C., sodium sulfite was added slowly to the reaction system so that the inner temperature of the reaction system maintained in a range of 15 to 19° C. until a starch paper did not detect hydrogen peroxide. Subsequently, sodium hydrogen carbonate was added slowly to adjust pH of the reaction liquid at 7.3 so that the inner temperature of the reaction system was maintained in a range of 15 to 17° C. The reaction liquid was extracted with ethyl acetate (900 g) twice, and the obtained organic layers were combined, washed with water (200 g), and then concentrated under the reduced pressure until the amount of the liquid became 138.3 g. Isopropyl ether (103.7 g) was added to the resultant concentrated liquid in a heated state at 50° C., then the reaction liquid was cooled down to 5° C. at a rate of about 10° C./hour, to precipitate crystal of the product. After filtering the precipitated crystal, the filtered out crystal was washed with isopropyl ether (50 g) at 5° C., and dried at 40° C. for 2 hours under the reduced pressure, to obtain 2-hydroxy-4-oxa-5-thiatricyclo[4.2.1.0$^{3,7}$]nonane 5,5-dioxide (53.9 g, purity: 99.1%, 0.281 mol). It should be noted that, yield of the product from 5-norbornene-2-sulfonyl chloride was 38.1%.

Example 3

Synthesis of 5-norbornene-2-sulfonyl chloride

By carrying out just same procedures as in Example 1, a filtrate (1657 g) (this filtrate is also referred to as "Filtrate B") was obtained. "Filtrate B" was analyzed by gas chromatography to confirm that 5-norbornene-2-sulfonyl chloride (184.3 g, 0.957 mol) was contained. It should be noted that, yield of 5-norbornene-2-sulfonyl chloride from 2-chloroethanesulfonyl chloride was 79.7%. In addition, endo/exo ratio of 5-norbornene-2-sulfonyl chloride contained in Filtrate B was 90/10.

Example 4-1

Synthesis of 2-hydroxy-4-oxa-5-thiatricyclo[4.2.1.0$^{3,7}$]nonane 5,5-dioxide using pyridine as a base Into a three-necked flask having an inner volume of 3 L equipped with a stirrer and a thermometer, water (750 g) and pyridine (250.0 g, 3.16 mol) were charged. "Filtrate B" (1300 g) (contains 5-norbornene-2-sulfonyl chloride (145.6 g, 0.751 mol)), which was obtained in the above-described Example 3, was added thereto with stirring, and the reaction system was stirred for further 10 hours while the inner temperature of the reaction system was maintained in a range of 35 to 40° C. The resultant reaction liquid was analyzed by gas chromatography to confirm that 5-norbornene-2-sulfonyl chloride was completely disappeared. The reaction liquid was concentrated under the reduced pressure to remove THF and pyridine. After that, the reaction liquid was transferred to a separating funnel of 2 L, washed with toluene (300 g) 3 times, to obtain an aqueous solution (918.8 g) containing pyridinium 5-norbornene-2-sulfonate (this aqueous solution is also referred to as "Aqueous Solution B"). It should be noted that, endo/exo ratio of pyridinium 5-norbornene-2-sulfonate contained in Aqueous Solution B was 80/20.

Into a three-necked flask having an inner volume of 2 L equipped with a stirrer, a thermometer and a dropping funnel, the whole amount of "Aqueous Solution B" obtained above was charged, and cooled down to 10° C. 99% Formic acid (93.27 g, 2.01 mol) was weighed and added dropwise to the reaction system so that the inner temperature of the reaction system was maintained in a range of 11 to 15° C. After that, the inner temperature was raised up to 50 to 53° C. by heating, and then 30% hydrogen peroxide aqueous solution (162.5 g, 1.43 mol) weighed and contained in another dropping funnel was added dropwise to the reaction system over 3 hours. After completion of the dropping, the inner temperature of the reaction system was also maintained at around 50° C. After 17 hours from completion of the dropping, the reaction liquid was analyzed by HPLC to confirm that conversion ratio of pyridinium 5-bornene-2-sulfonate was 99.0%. After cooling down the reaction liquid to 15° C., sodium sulfite was added slowly to the reaction system so that the inner temperature of the reaction system was maintained in a range of 15 to 18° C. until a starch paper did not detect hydrogen peroxide. Subsequently, sodium hydrogen carbonate was added slowly to adjust pH of the reaction liquid at 7.5 so that the inner temperature of the reaction system was maintained in a range of 17 to 20° C. The reaction liquid was extracted with ethyl acetate (900 g) twice, and the resultant organic layers were combined, washed with water (200 g), and then concentrated under the reduced pressure until the amount of the liquid became 226.9 g. Isopropyl ether (169.5 g) was added to the resultant concentrated liquid in a heated state at 50° C., then the mixture was cooled down to 5° C. at a rate of about 10° C./hour, to precipitate crystal of the product. After filtering the precipitated crystal, the filtered out crystal was washed with isopropyl ether (50 g) at 5° C., and dried at 40° C. for 2 hours under the reduced pressure, to obtain 2-hydroxy-4-oxa-5-thiatricyclo[4.2.1.0$^{3,7}$]nonane 5,5-dioxide (88.8 g, purity:

99.0%, 0.462 mol). It should be noted that, yield of the product from 5-norbornene-2-sulfonyl chloride was 61.5%.

Example 4-2

Synthesis of 2-hydroxy-4-oxa-5-thiatricyclo[4.2.1.0$^{3,7}$]nonane 5,5-dioxide using 2-methylpyridine as a base Into a three-necked flask having an inner volume of 300 mL equipped with a stirrer and a thermometer, water (65.4 g) and 2-methlpyridine (21.8 g, 0.234 mol) were charged. "Filtrate B" (150.0 g) (contains 5-norbornene-2-2sulfonyl chloride (16.7 g, 0.087 mol)), which was obtained in the above-described Example 3, was added thereto with stirring, and the reaction system was stirred for further 13 hours while the inner temperature of the reaction system was maintained at 50° C. The resultant reaction liquid was analyzed by gas chromatography to confirm that conversion ratio of 5-norbornene-2-sulfonyl chloride was 93.2%. The reaction liquid was concentrated under the reduced pressure to remove THF and 2-methylpyridine. After that, the reaction liquid was transferred to a separating funnel of 300 mL, and washed with toluene (35 g) 3 times, to obtain an aqueous solution (82.1 g) containing 2-methylpyridinium 5-norbornene-2-sulfonate (this aqueous solution is also referred to as"Aqueous Solution C"). It should be noted that, endo/exo ratio of 2-methylpyridinium 5-norbornene-2-sulfonate contained in Aqueous Solution C was 81/19.

Into a three-necked flask having an inner volume of 300 mL equipped with a stirrer, a thermometer and a dropping funnel, the whole amount of "Aqueous Solution C" obtained above was charged, and cooled down to 10° C. 99% Formic acid (10.8 g, 0.232 mol) was weighed into a dropping funnel, and added dropwise to the reaction system so that the inner temperature of the reaction system was maintained in a range of 11 to 15° C. After that, the inner temperature was raised up to 50 to 52° C. by heating, and then 30% hydrogen peroxide aqueous solution (18.69 g, 0.165 mol) weighed and contained in another dropping funnel was added dropwise to the reaction system over 3 hours. After completion of the dropping, the inner temperature of the reaction system was also maintained at around 50° C. After 21 hours from completion of the dropping, the reaction liquid was analyzed by HPLC to confirm that conversion ratio of 2-methylpyridinium 5-bornene-2-sulfonate was 98.1%. After cooling down the reaction liquid to 15° C., sodium sulfite was added slowly to the reaction system so that the inner temperature of the reaction system was maintained in a range of 15 to 18° C. until a starch paper did not detect hydrogen peroxide. Subsequently, sodium hydrogen carbonate was added slowly to adjust pH of the reaction liquid at 7.0 so that the inner temperature of the reaction system was maintained in a range of 17 to 20° C. The reaction liquid was extracted with ethyl acetate (100 g) twice, the resultant organic layers were combined, washed with water (25 g), and then concentrated under the reduced pressure until the amount of the liquid became 35.1 g. Isopropyl ether (21.0 g) was added to the resultant concentrated liquid in a heated state at 50° C., then the mixture was cooled down to 5° C. at a rate of about 10° C./hour, to precipitate crystal of the product. After filtering the precipitated crystal, the filtered out crystal was washed with isopropyl ether (6.0 g) at 5° C., and dried at 40° C. for hours under the reduced pressure, to obtain 2-hydroxy-4-oxa-5-thiatricyclo[4.2.1.0$^{3,7}$]nonane 5,5-dioxide (8.74 g, purity: 98.6%, 0.045 mol). It should be noted that, yield of the product from 5-norbornene-2-sulfonyl chloride was 52.3%.

Example 4-3

Synthesis of 2-hydroxy-4-oxa-5-thiatricyclo[4.2.1.0$^{3,7}$]nonane 5,5-dioxide using 2,6-dimethylpyridine as a base Into a three-necked flask having an inner volume of 300 mL equipped with a stirrer and a thermometer, water (75.2 g) and 2,6-dimethlpyridine (25.1 g, 0.234 mol) were charged. "Filtrate B" (150.0 g) (contains 5-norbornene-2-sulfonyl chloride (16.7 g, 0.087 mol)), which was obtained in the above-described Example 3, was added thereto with stirring, and the reaction system was stirred for further 19 hours while the inner temperature of the reaction system was maintained at 50° C. The resultant reaction liquid was analyzed by gas chromatography to confirm that conversion ratio of 5-norbornene-2-sulfonyl chloride was 90.0%. The reaction liquid was concentrated under the reduced pressure to remove THF and 2,6-dimethylpyridine. After that, the reaction liquid was transferred to a separating funnel of 300 mL, and washed with toluene (35 g) 3 times, to obtain an aqueous solution (90.8 g) containing 2,6-dimethylpyridinium 5-norbornene-2-sulfonate (this aqueous solution is also referred to as "Aqueous Solution D"). It should be noted that, endo/exo ratio of 2,6-dimethylpyridinium 5-norbornene-2-sulfonate contained in Aqueous Solution D was 83/17.

Into a three-necked flask having an inner volume of 300 mL equipped with a stirrer, a thermometer and a dropping funnel, the whole amount of "Aqueous Solution D" obtained above was charged, and cooled down to 10° C. 99% Formic acid (10.8 g, 0.232 mol) was weighed into a dropping funnel, and added dropwise to the reaction system so that the inner temperature of the reaction system was maintained in a range of 11 to 15° C. After that, the inner temperature was raised up to 50 to 52° C. by heating, and then 30% hydrogen peroxide aqueous solution (18.69 g, 0.165 mol) weighed and contained in another dropping funnel was added dropwise to the reaction system over 3 hours. After completion of the dropping, the inner temperature of the reaction system was also maintained at around 50° C. After 21 hours from completion of the dropping, the reaction liquid was analyzed by HPLC to confirm that conversion ratio of 2,6-dimethylpyridinium 5-bornene-2-sulfonate was 98.4%. After cooling down the reaction liquid to 15° C., sodium sulfite was added slowly to the reaction system so that the inner temperature of the reaction system was maintained in a range of 15 to 18° C. until a starch paper did not detect hydrogen peroxide. Subsequently, sodium hydrogen carbonate was added slowly to adjust pH of the reaction liquid at 7.0 so that the inner temperature of the reaction system was maintained in a range of 17 to 20° C. The reaction liquid was extracted with ethyl acetate (100 g) twice, the resultant organic layers were combined, and washed with water (25 g), then concentrated under the reduced pressure until the amount of the liquid became 37.4 g. Isopropyl ether (21.0 g) was added to the resultant concentrated liquid in a heated state at 50° C., then the mixture was cooled down to 5° C. at a rate of about 10° C./hour, to precipitate crystal of the product. After filtering the precipitated crystal, the filtered out crystal was washed with isopropyl ether (6.0 g) at 5° C., and dried at 40° C. for hours under the reduced pressure, to obtain 2-hydroxy-4-oxa-5-thiatricyclo[4.2.1.0$^{3,7}$]nonane 5,5-dioxide (7.86 g, purity: 98.1%, 0.041 mol). It should be noted that, yield of the product from 5-norbornene-2-sulfonyl chloride was 46.8%.

Example 5

Synthesis of 7-oxa-5-norbornene-2-sulfonyl chloride

Into a four-necked flask having an inner volume of 500 mL equipped with a stirrer and a thermometer, furan (167 g, 2.45 mol) was charged. Subsequently, 2-chloroethanesulfonyl chloride (50.0 g, 0.307 mol) and a mixed liquid of triethylamine (37.5 g, 0.371 mol) and furan (34.1 g, 0.501 mol) were each weighed into separate dropping funnels, and added dropwise to the mixture simultaneously at the inner temperature of 25 to 28° C. over 4 hours. After completion of the dropping, the reaction mixture was stirred at 25 to 28° C. for further 7 hours, and then water (125 g) was added. The reaction mixture was divided into two layers, and the lower layer (this lower layer was also referred to as "Organic Layer E") was separated. Organic layer E was analyzed by HPLC to confirm that 7-oxa-5-norbornene-2-sulfonyl chloride (48.3 g, 0.248 mol) was contained. It should be noted that, yield of 7-oxa-5-norbornene-2-sulfonyl chloride from 2-chloroethanesulfonyl chloride was 80.8%. Further, endo/exo ratio of 7-oxa-5-norbornene-2-sulfonyl chloride contained in Organic layer E was 69/31.

Example 6

Synthesis of 2-hydroxy-4,8-dioxa-5-thiatricyclo [4.2.1.0$^{3,7}$]nonane 5,5-dioxide using sodium hydroxide as a base Into a three-necked flask having an inner volume of 1 L equipped with a stirrer, a thermometer and a dropping funnel, water (221.4 g) was charged, and cooled down to 20° C. or lower. Sodium hydroxide (24.6 g, 0.614 mol) was added thereto with stirring so that the inner temperature was maintained at 20° C. or lower. "Organic Layer E" (contained 7-oxa-5-norbornene-2-sulfonyl chloride (endo/exo ratio=69/31) (48.3 g, 0.248 mol)), which was obtained in the above-described Example 5, was charged into a dropping funnel, and this Organic layer E was added dropwise to the reaction system over 4 hours so that the inner temperature of the reaction system was maintained in a range of 16 to 19° C. After 1 hour from completion of the dropping, the reaction liquid was analyzed by HPLC to confirm that 7-oxa-5-norbornene-2-sulfonyl chloride was completely disappeared. The reaction liquid was transferred to a separating funnel of 1 L, and left for 1 hour. The reaction liquid was divided into two layers, and the lower layer was separated, and concentrated under the reduced pressure at 40° C. to remove furan (thus obtained liquid is also referred to as "Concentrated Liquid F"). It should be noted that, endo/exo ratio of sodium 7-oxa-5-norbornene-2-sulfonate contained in Concentrated Liquid F was 39/61.

Into a three-necked flask having an inner volume of 500 mL equipped with a stirrer, a thermometer and a dropping funnel, the whole amount of "Concentrated Liquid F" obtained above was charged, and cooled down to 10° C. 99% Formic acid (30.0 g, 0.645 mol) was weighed into a dropping funnel, and added dropwise to the reaction system so that the inner temperature of the reaction system was maintained in a range of 15 to 18° C. After that, the inner temperature was raised up to 34 to 35° C. by heating, and then 30% hydrogen peroxide aqueous solution (45.2 g, 0.399 mol) weighed and contained in another dropping funnel was added dropwise to the reaction system over 3 hours. After completion of the dropping, the inner temperature of the reaction system was also maintained at around 35° C. After 40 hours from completion of the dropping, the reaction liquid was analyzed by HPLC to confirm that conversion ratio of sodium 7-oxa-5-bornene-2-sulfonate was 98.1%. After cooling down the reaction liquid to 20° C., sodium sulfite was added slowly to the reaction system so that the inner temperature of the reaction system was maintained in a range of 20 to 25° C. until a starch paper did not detect hydrogen peroxide. Subsequently, 30% sodium hydroxide aqueous solution was added slowly to adjust pH of the reaction liquid at 6.8 so that the inner temperature of the reaction system was maintained in a range of 20 to 25° C. The reaction liquid was extracted with ethyl acetate (100 g) three times, and the resultant organic layers were combined, washed with water (50 g), and then concentrated under the reduced pressure until forming of white solid could be seen. Ethyl acetate (20 g) was added, and then isopropyl ether (40 g) as also added in a heated state at 60° C., then the mixture was cooled down to 1° C. at a rate of about 15° C./hour, to precipitate crystal of the product. After filtering the precipitated crystal, the filtered out crystal was washed with isopropyl ether (40 g) at 1° C., and dried at 30° C. for 2 hours under the reduced pressure, to obtain 2-hydroxy-4,8-dioxa-5-thiatricyclo[4.2.1.0$^{3,7}$]nonane 5,5-dioxide (6.84 g, purity: 98.9%, 0.035 mol). It should be noted that, yield of the product from 7-oxa-5-norbornene-2-sulfonyl chloride was 14.2%.

Comparative Example 1

Synthesis of methyl 5-norbornene-2-sulfonate

According to the example of synthesis described in Angew. Chem., 77(7), 291-302 (1965), methyl vinylsulfonate was synthesized. Specifically, firstly, into a four-necked flask having an inner volume of 2 L equipped with a stirrer, a thermometer and a dropping funnel, 2-chloroethanesulfonyl chloride (326.0 g, 2.00 mol) was charged under the nitrogen atmosphere, and cooled in an ice bath. Subsequently, sodium methoxide (25% by mass, methanol solution) (864.3 g, 4.00 mol) was added dropwise from a dropping funnel so that the inner temperature of the reaction system was maintained in a range of 2 to 5° C. After completion of the dropping, the ice bath was removed and the reaction liquid was stirred at room temperature for 1 hour. The reaction liquid was filtered, the filtrate was concentrated under the reduced pressure, and the concentrate was subjected to a simple distillation procedure, to obtain methyl vinylsulfonate (197.2 g, purity: 97.3%, 1.571 mol). It should be noted that, yield of methyl vinylsulfonate from 2-chloroethanesulfonyl chloride was 78.5%.

Subsequently, according to Example 1 described in JP-A-2007-31355, methyl 5-norbornene-2-sulfonate was synthesized. Into a four-necked flask having an inner volume of 5 L equipped with a stirrer, a thermometer and a reflux condenser, toluene (2000 g), cyclopentadiene (225 g, 3.40 mol), and then methyl vinylsulfonate (100 g, purity: 97.3%, 0.82 ml) were charged, and stirring and heating were initiated to react under reflux for 4 hours. By concentrating the reaction liquid under the reduced pressure, methyl 5-norbornene-2-sulfonate (128.8 g, purity was 92.1% as a peak area percentage in gas chromatography analysis) was obtained.

Comparative Example 2

Synthesis of 2-hydroxy-4-oxa-5-thiatricyclo[4.2.1. 0$^{3,7}$]nonane 5,5-dioxide

According to Example 1 described in JP-A-2007-31355, 2-hydroxy-4-oxa-5-thiatricyclo[4.2.1.0$^{3,7}$]nonane 5,5-dioxide was synthesized. Specifically, firstly, into a four-necked flask having an inner volume of 5 L equipped with a stirrer, a thermometer and a dropping funnel, methyl 5-norbornene-2-sulfonate (128.8 g, purity: 92.1%) which was obtained in the above-described Comparative Example 1 and methylene chloride (2650 g) were charged. m-Chlorobenzoic acid (200.0 g) was charged slowly under stirring in a state cooled with an ice bath so that the inner temperature of the reaction system did not rise to 5° C. or higher. After confirming disappearance of methyl 5-norbornene-2-sulfonate, 20% by mass sodium sulfite aqueous solution (687.1 g) was added dropwise so that the inner temperature of the reaction system was maintained in a range of 5 to 10° C. After that, the organic layer was washed with a saturated sodium hydrogen carbonate aqueous solution (500 g) three times. By concentrating the resultant organic layer under the reduced pressure, methyl 5,6-epoxynorbornane-2-sulfonate (125.9 g, purity was 87.2% as a peak area percentage in gas chromatography analysis) was obtained.

Into a four-necked flask having an inner volume of 2 L equipped with a stirrer, a thermometer and a dropping funnel, a 5 mol/L sodium hydroxide aqueous solution (400 mL) was charged. Methyl 5,6-epoxynorbornane-2-sulfonate (125.9 g, purity: 87.2%) was added dropwise from a dropping funnel while the reaction system was cooled with a water bath so that the inner temperature of the reaction system did not exceed 30° C. After completion of the dropping, the reaction liquid was stirred at room temperature for further 5 hours. After that, 5 mol/L of hydrochloric acid (400 mL) was added dropwise while the reaction system was cooled with an ice bath so that the inner temperature of the reaction system did not exceed 30° C. to neutralize the reaction system. The reaction liquid was extracted with methylene chloride (800 g) three times, and the obtained organic layers were combined and concentrated under the reduced pressure, to obtain the concentrate (65.9 g).

For the resultant concentrate, crystallization was tried using various solvents such as ethyl acetate, ethyl acetate-isopropyl ether mixed solution, methanol-isopropyl ether mixed solution, and the like, but no crystallized product could be obtained. Subsequently, by purifying the resultant concentrate by a silica gel chromatography (developing solvent was hexane:ethyl acetate=1:1 (volume ratio)), 2-hydroxy-4-oxa-5-thiatricyclo[4.2.1.0$^{3,7}$]nonane 5,5-dioxide (39.8 g, purity: 99.2%, 0.214 mol) was obtained. It should be noted that, yield of the product from methyl 5-norbornene-2-sulfonate was 34.0%.

From the results shown in the above-described Examples 2 and 4 as well as Comparative Example 2, it can be understood that according to the production method of the present invention, a highly pure 2-hydroxy-4-oxa-5-thiatricyclo[4.2.1.0$^{3,7}$]nonane 5,5-dioxide derivative can be produced industrially in high yield from highly pure and industrially available raw materials.

The invention claimed is:

1. A production method for a sultone derivative of chemical formula 2 described below, comprising:
(A) hydrolyzing a sulfonyl halide derivative of chemical formula 1:

[Chemical Formula 1]

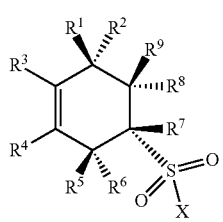

wherein $R^1$ to $R^9$ each independently represent a hydrogen atom, an alkyl group having 1 to 10 carbon atoms, a cycloalkyl group having 3 to 10 carbon atoms or an alkoxy group having 1 to 10 carbon atoms, or $R^1$ and $R^5$ are bound together and form an alkylene group having 1 to 6 carbon atoms and optionally comprising an oxygen atom or a sulfur atom; and X represents a fluorine atom, a chlorine atom or a bromine atom;

or an enantiomer thereof, and (B) reacting said hydrolyzed sulfonyl halide derivative with an oxidizing agent to obtain a corresponding sultone derivative of chemical formula 2:

[Chemical Formula 2]

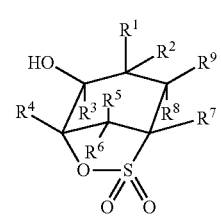

or an enantiomer thereof.

2. The production method according to claim 1, wherein the hydrolysis in the step (A) is carried out in the presence of a base.

3. The production method according to claim 2, wherein the base is a nitrogen-containing aromatic compound.

4. The production method according to claim 1, wherein $R^1$ and $R^5$ are bound together to represent a methylene group, —O— or —S—.

5. The production method according to claim 1, further comprising a step to obtain a sulfonyl halide derivative of chemical formula 1, comprising carrying out a Diels-Alder reaction of a diene derivative of chemical formula 8:

[Chemical Formula 8]

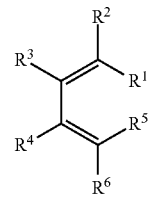

wherein $R^1$ to $R^6$ each independently represent a hydrogen atom, an alkyl group having 1 to 10 carbon atoms, a cycloalkyl group having 3 to 10 carbon atoms or an alkoxy group having 1 to 10 carbon atoms, or $R^1$ and $R^5$ are bound together and form an alkylene group having 1 to 6 carbon atoms and optionally comprising an oxygen atom or a sulfur atom;

and a vinylsulfonyl halide of chemical formula 10:

[Chemical Formula 10]

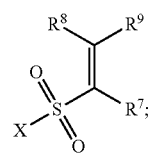

and
said vinylsulfonyl halide is obtained by a dehydrohalogenation reaction of a dihalide of chemical formula 9:

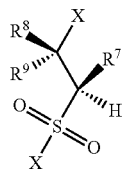

[Chemical Formula 9]

wherein $R^7$ to $R^9$ each independently represent a hydrogen atom, an alkyl group having 1 to 10 carbon atoms, a cycloalkyl group having 3 to 10 carbon atoms or an alkoxy group having 1 to 10 carbon atoms; and X represents a fluorine atom, a chlorine atom, or a bromine atom.

6. The production method according to claim 5, wherein said diene derivative of chemical formula 8 and said dihalide of chemical formula 9 are reacted in the presence of a base.

7. The production method according to claim 6, wherein the reaction is carried out by adding said dihalide of chemical formula 9 and a base to said diene derivative of chemical formula 8.

* * * * *